United States Patent
Saul et al.

(10) Patent No.: US 11,173,289 B2
(45) Date of Patent: Nov. 16, 2021

(54) PROGRAMMABLE CSF METERING SHUNT

(71) Applicant: CSF Refresh Inc., Redmond, WA (US)

(72) Inventors: Tom Saul, Moss Beach, CA (US); Kristof Hovaten, San Bruno, CA (US)

(73) Assignee: CSF Refresh, Inc., Redmond, WA (US)

( * ) Notice: Subject to any disclaimer, the term of this patent is extended or adjusted under 35 U.S.C. 154(b) by 215 days.

(21) Appl. No.: 16/242,793

(22) Filed: Jan. 8, 2019

(65) Prior Publication Data
US 2019/0175884 A1  Jun. 13, 2019

Related U.S. Application Data

(63) Continuation of application No. 15/288,273, filed on Oct. 7, 2016, now Pat. No. 10,201,686, which is a
(Continued)

(51) Int. Cl.
*A61M 27/00* (2006.01)
*F16K 99/00* (2006.01)

(52) U.S. Cl.
CPC ....... *A61M 27/006* (2013.01); *F16K 99/0015* (2013.01); *F16K 99/0057* (2013.01);
(Continued)

(58) Field of Classification Search
CPC .............. A61M 27/006; A61M 27/002; A61M 2205/3334; A61M 2205/3344;
(Continued)

(56) References Cited

U.S. PATENT DOCUMENTS

| 3,768,508 A | 10/1973 | Schulte |
| 3,901,245 A | 8/1975 | Spitz et al. |

(Continued)

FOREIGN PATENT DOCUMENTS

WO   WO-2015157334 A1   10/2015

OTHER PUBLICATIONS

"Extended European Search Report and Search Opinion dated Nov. 23, 2017 for European Patent Application No. 15776975.3".
(Continued)

*Primary Examiner* — Philip R Wiest
(74) *Attorney, Agent, or Firm* — Wilson Sonsini Goodrich & Rosati

(57) ABSTRACT

An implantable body fluid drainage system includes a metering shunt having a housing with an internal chamber. A movable barrier divides the chamber into a first section and a second section, and the barrier can be displaced by a differential pressure. A first powered inlet valve providing a fill path to the first section of the chamber, and a first powered drain valve providing a drain path from the first section of the chamber. A CSF inlet conduit connects a CSF space to the first powered inlet valve. A CSF outlet conduit connects the first powered outlet valve to a discharge location. A controller opens the first powered inlet valve and close the first powered drain valve to fill the first section to a volume defined by the barrier and chamber geometry and closes the first powered inlet valve and opens the first powered drain valve to discharge the filled volume from the first section through the outlet conduit.

8 Claims, 18 Drawing Sheets

Related U.S. Application Data continuation of application No. PCT/US2015/024779, filed on Apr. 7, 2015.

(60) Provisional application No. 61/976,464, filed on Apr. 7, 2014.

(52) U.S. Cl.
CPC ............ *A61M 2205/3334* (2013.01); *A61M 2205/3344* (2013.01); *A61M 2205/52* (2013.01); *A61M 2205/8206* (2013.01); *F16K 2099/0088* (2013.01)

(58) Field of Classification Search
CPC ...... A61M 2205/52; A61M 2205/8206; A61B 5/031; F16K 99/0015; F16K 99/0057; F16K 2099/0088
See application file for complete search history.

(56) References Cited

U.S. PATENT DOCUMENTS

| | | | |
|---|---|---|---|
| 4,741,730 | A | 5/1988 | Dormandy, Jr. et al. |
| 6,090,062 | A | 7/2000 | Sood et al. |
| 6,689,085 | B1 | 2/2004 | Rubenstein et al. |
| 7,025,739 | B2 * | 4/2006 | Saul ............ A61B 5/031 604/8 |
| 10,201,686 | B2 | 2/2019 | Saul et al. |
| 2003/0004495 | A1 | 1/2003 | Saul |
| 2010/0056980 | A1 | 3/2010 | Negre et al. |
| 2011/0004158 | A1 | 1/2011 | Luciano et al. |
| 2012/0226215 | A1 | 9/2012 | Hsu et al. |

OTHER PUBLICATIONS

"International search report and written opinion dated Jul. 7, 2015 for PCT Application US-2015024779".

"U.S. Appl. No. 15/288,273 Office Action dated Mar. 9, 2018".

* cited by examiner

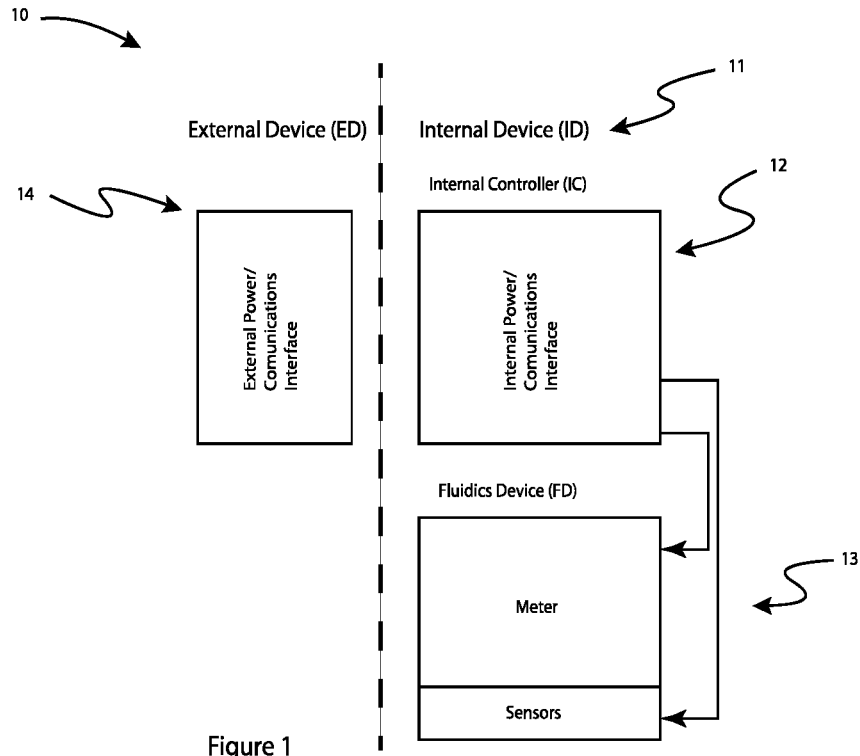
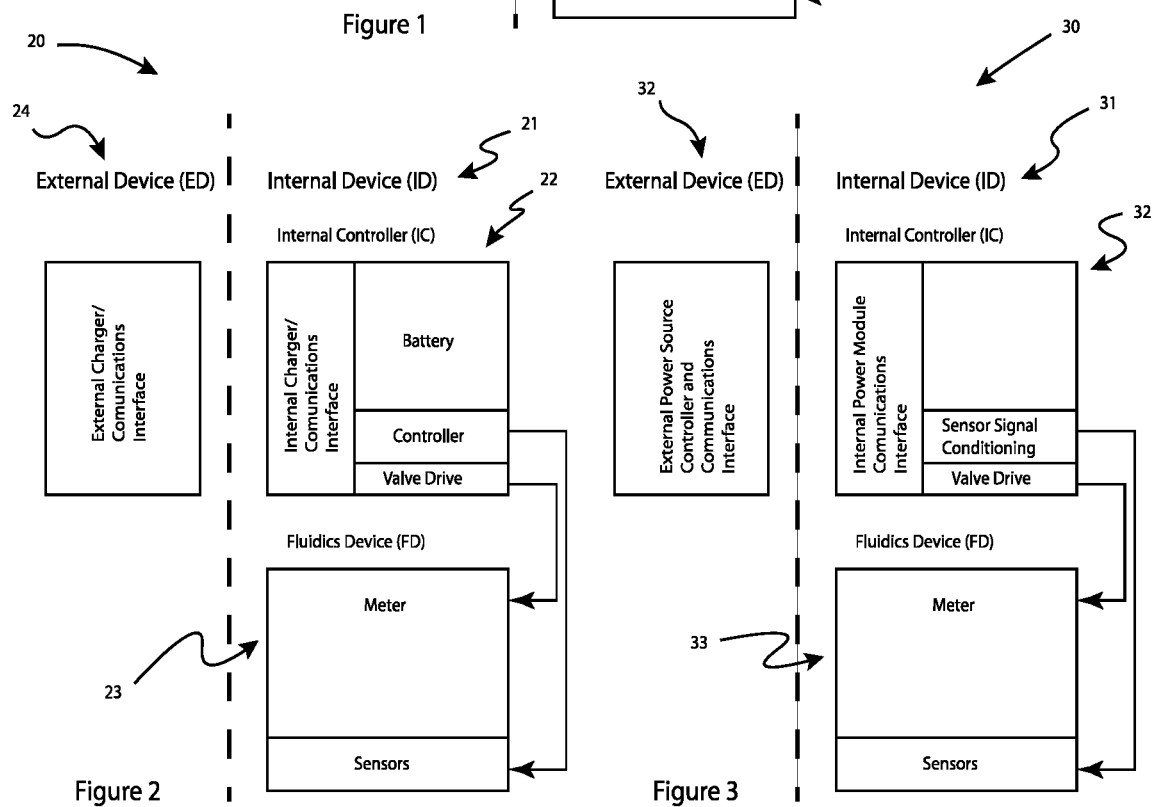

State I: Rest
Valve a: No flow
Valve b: No flow

State II: Transfer
Valve a: No flow
Valve b: Flow

State III: Recover
Valve a: Flow
Valve b: No flow

| State | Valve a | Valve b | Outcome |
|-------|---------|---------|---------------|
| I     | closed  | closed  | No flow       |
| II    | open    | closed  | equilibrate A/B |
| III   | closed  | open    | empty B       |
| IV    | open    | open    | disallowed    |
Figure 8
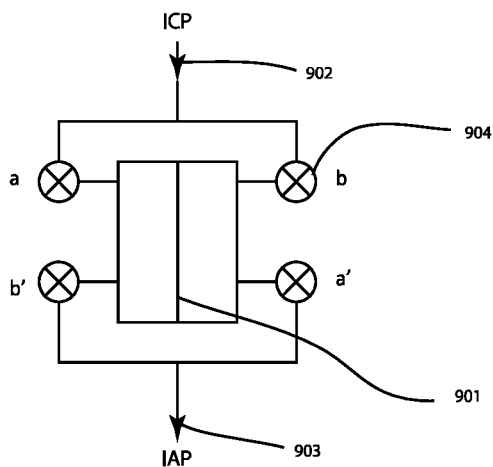
Figure 9A
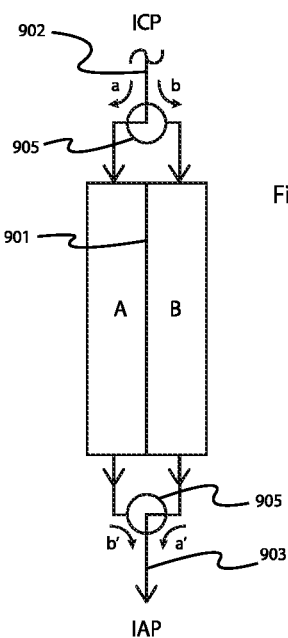
Figure 9B
Figure 9C
| FLOW | a | b | a' | b' |
|------|------|------|------|------|
| empty B - fill A | open | closed | open | closed |
| fill B - empty A | closed | open | closed | open |

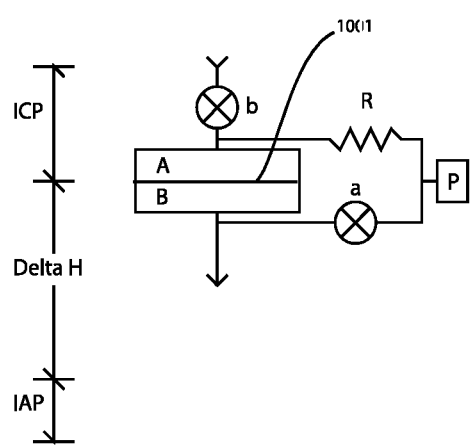
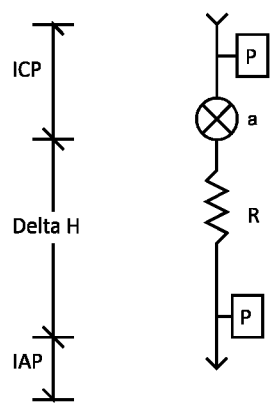
Figure 10                           Figure 11

PROGRAMMABLE CSF METERING SHUNT

CROSS-REFERENCE TO RELATED APPLICATIONS

This application is a continuation of U.S. patent application Ser. No. 15/288,273, filed Oct. 7, 2016, which is a continuation of PCT Application No. PCT/US2015/024779, filed Apr. 7, 2015, which claims the benefit of U.S. Provisional Application No. 61/976,464, filed Apr. 7, 2014, the entire content of which are incorporated herein by reference.

BACKGROUND OF THE INVENTION

Normal Pressure Hydrocephalus (NPH) and Alzheimer's Disease (AD) constitute an important public health crisis and may be treated by shunting. However, shunt treatment in NPH has resulted in mixed outcomes and the current treatment has the following problems. Not all patients improve with shunting, using the standard pressure controlling shunts, and, if improvement does occur, it often dissipates in a few years' time. Over-shunting and under-shunting in NPH have been significant clinical problems despite the development of programmable shunts capable of multiple opening pressure settings. AD may also be treated by shunting, but clinical trials have failed to ID 11 entify a therapeutic that alters the progression of disease. Cognitive impairment in NPH and AD is linked to amyloid-beta peptide (Aβ) accumulation and the "amyloid cascade" (Querfurth and LaFerla 2010; Silverberg et al. BRES 2010; Silverberg et al. Lancet Neurol 2003). In aging, NPH and AD there is no increase in Aβ production; rather, Aβ clearance from the brain declines (Mawuenyega et al. 2010; Silverberg et al BRES 2010; Silverberg et al J Neurosurg 2002). Improving Cerebrospinal Fluid (CSF) turnover and metabolite clearance could significantly benefit both NPH and AD patients. Aging is the single most important risk factor in the genesis of AD (NIH 2002, Lu 2004, Yankner 2008), and ID 11 iopathic NPH is a disease of elderly patients. A number of Aβ clearance pathway defects as a function of age that play a role in age-dependent Aβ accumulation have been ID 11 entified (Silverberg et al. 2003, 2010a, 2010b, Pascale et al. 2011; Chiu et al. 2012). Aβ transport at the brain barriers, the blood-brain barrier (BBB) and the blood-CSF barrier (BCSFB) is impaired due to age, NPH- and AD-dependent alterations in Aβ transporter expression, decreases CSF production and turnover rates (May et al. 1990, Preston 2001, Silverberg et al. 2001, 2002, 2003, Chiu et al 2012). Improved CSF dynamics in mitigating cognitive decline in these dementias may define a new and more effective treatment option for NPH and AD, and perhaps other proteinopathies as well. Such novel therapy is an urgent public health necessity.

CSF shunt designs and functionality have changed little since their introduction some 50 years ago. They are designed to regulate Intracranial Pressure (ICP) by providing an alternative pathway for CSF to escape from the Central Nervous System (CNS) under the control of a valve, typically "shunting" CSF from one of the lateral ventricles to the peritoneal cavity. The vast majority of traditional available shunts operate as passive pressure relief valves. One notable exception is a hybrid which operates as a pressure relief valve at physiologically low and high pressures and as a flow control (variable resistance valve) over the "normal" range of pressures. A number of the pressure control devices are magnetically-adjustable in that their performance characteristics, the rate of flow as a function of pressure, can be modified after implantation to one of a predetermined number of settings. None of these devices incorporates any means of monitoring shunt outflow nor do they provide information on clinically-significant parameters to clinicians. Assessment of shunt function is difficult as there are currently no means, separate from invasive techniques, to measure pressure or flow through implanted shunts. Their outflow is dependent on patient specific boundary conditions which affect the pressure differential between the input and output of the device. These include conditions such as posture, level of physical activity, sleep (REM) and changes in CSF production. As such, no device available today is capable of draining a known and consistent volume of CSF, or of performing real time modification of performance to accommodate different and or varying patient specific boundary conditions. Pumps and meters are capable of transferring a consistent volume of CSF, independent of patient specific boundary conditions, and may provide a significant advantage over traditional shunts. The primary challenges associated with bringing such devices to market are minimizing power requirements and miniaturization.

NPH is now often treated by CSF shunting and clinical trials have been run to evaluate the efficacy of treating AD by shunting. However in NPH, CSF pressure is normal for much of the time, and in AD it is entirely normal or low. Given the highly variable flow rates associated with traditional shunt performance which are dependent upon the CSF pressure, the valve opening pressure and the conductance of the shunt system 20, results from such usage and trials has been varied. Interestingly, NPH patients implanted with low resistance shunts (those likely to have higher flow rates) have a better outcome than those implanted with higher pressure valves, but at the same time have a higher incidence of subdural fluid collections, a sign of over-shunting (Boone et al. 1998).

By improved control of CSF outflow and incumbent improvement in CSF circulation, a novel shunt system may relieve or reduce the symptoms and suffering of these patients. Currently available shunt systems focus on maintaining a normal ICP with no acknowledgment of the CSF flow rate, whereas novel new shunts as described herein will focus on maintaining normal or improved CSF flow and turnover rates while still monitoring ICP. Turnover is defined as the number of times the total volume of CSF is replaced in a day, which is normally four to five times daily. CSF turnover is a major pathway for clearance of potentially toxic metabolites from the brain, e.g., amyloid and tau protein, particularly important when transport across the brain capillaries becomes less efficient with age.

Currently available shunt systems also lack diagnostic and control capabilities that can be performed by an actively powered and programmable shunt system with appropriate sense inputs. Such sense inputs comprise relevant physiological parameters such as but not limited to parenchymal perfusion, CNS compliance, CSF production, and O2 saturation. They are additionally unable to differentiate between ICP, hydrostatic head (HH), and outflow pressure. This is significant because HH and outflow pressure have little clinical relevance to the treatment and often constitute a source of error and clinical risk. Currently available shunt systems also lack the ability to measure or treat on the basis of CNS compliance, brain perfusion, and other associated characteristic such as CNS frequency response. They lack the means to modify performance as a function of time of day or the outcome of previous treatments. They also lack a means of communicating clinically relevant data to a clinician, such as patient diagnostics, shunt performance, or the occlusion of the shunt. Currently available "programmable" shunts only provide a means to switch between a set of predetermined flow-pressure performance curves and do not address these concerns.

SUMMARY OF THE INVENTION

Devices and methods of the present invention provide for the programmable volumetric transfer of cerebrospinal fluid (CSF) from the central nervous system (CNS) of a patient. The devices and methods are particularly intended for the treatment of hydrocephalus, Alzheimer's disease, and other conditions, which are caused by, or are otherwise related to the retention of CSF, the excessive accumulation of toxic and other substances in the CSF, and the impaired circulation of CSF. A controllable device for the treatment of these diseases through CSF manipulation is comprised of any combination of the characteristics and capabilities described herein.

Volumetric transfer of CSF may be mediated by a CSF meter. A CSF meter is defined herein as a device which uses the pressure differential between the CNS and a drainage location to drive the transfer a known volume of CSF in a controlled manner. Control of the meter and flow may be achieved by the use of valves to prevent flow and/or alter the driving pressure differential. The transfer volume of the meter may be determined by mechanically constraining the transferred volume to a known and constant amount or by monitoring and recording a variable flow through the meter.

A primary challenge associate with meters is the ability to store and or provide the power required to operate the valves which constitute active components of the device. Power consumption is a critical design parameter which is addressed by the meter designs discussed herein. Meters with valves can lower overall power consumption when compared with pumps because the transfer of fluid is driven by naturally available physiological pressure gradients as opposed to a pump which is usually battery or externally powered and requires power to move the fluid.

Meters according to the present invention may comprise elastic and inelastic materials used to form features including chambers, diaphragms, and valves. Chambers formed partially or entirely of elastic materials will increase the compliance of the device and may have functional displacements associated with changes in fluid pressure. One embodiment of such a structure is two chambers divided by an elastic diaphragm. In this embodiment, the position of the elastic diaphragm is a function of the pressure differential across it, and the displacement of the diaphragm may be used to seal an orifice and/or to displace a fluid. Two of these structures in different diameters may be connected to create a piston with an associated pressure attenuation.

The device may incorporate one or more of the following actively powered valves. Valves may be actuated by a material phase change such as a thermal deformation of a solid, such as Nitinol® or nylon. This shape change can be used to operate a slit valve by deforming a membrane in a manner which increases or decreases the size of an orifice. Alternatively, the thermal deformation of a solid can be used to displace a valve seal formed by two faces and an orifice, such as a poppet valve. Both slit valves and poppet valves have embodiments which are either closed or open in an un-energized state. Additionally, the thermal deformation of solids can be used to actuate latches or ratchets, which may mechanically constrain or lock a valve in a specific state thereby creating a latching valve.

A valve may be operated by the thermal expansion of an inductively, resistively, or conductively heated fluid, such as silicone oil, contained within a deformable volume. In such a device, the deformation of the fluid volume would be associated with a change in valve state. This could be achieved by the obstruction or opening of an orifice or the constriction of a flow path.

A valve may be operated by a pump driven transfer of fluid in or out of a deformable volume from an external location. A thermal or electrical expansion of a hydrogel constrained within deformable volume may also be used to operate a valve. Passive check valves may also be incorporated in the form of slit valves or pre-stressed diaphragm valves, and may prevent siphoning or the backflow of CSF.

Positive displacement pumps may be used to pump a working fluid to operate a valve. A pump may be actuated by the thermal deformation of a solid, such a Nitinol® or nylon. The thermal deformation of a fluid such as silicone oil and/or the thermal or electrical deformation of a hydrogel may be used to drive a working fluid. An electro-osmotic or electro static pumps may also be used to pump a working fluid.

The device control inputs may include one or more of the following sense inputs and/or the parameters derived from these inputs. Pressure inputs include inter-cranial pressure (ICP), hydrostatic head (HH), valve outflow pressure, and shunt outflow pressure. $O_2$ saturation or tissue perfusion inputs which may be determined by optical plethysmography. Time inputs include time of day, duration of operation, or duration of in operation. Heart rate and respiration which may be determined via plethysmography or pressure variations in the CSF pressure waveform. CNS compliance may also be derived from the measurement of CSF pressure as a function of drained volume, or CSF production as a function of pressure recovery time after a known volume of CSF is drained via a modified Masserman technique. Position may be determined by an accelerometer, hydrostatic head, or both. Internal operating states include the position of a movable barrier of diaphragm. Sensors used to acquire these inputs may include any or any combination of the following, optical detectors, optical emitters, pressure sensors, accelerometers, proximity sensors.

The device operational modes may include one or a combination of the following. The device may operate in a primarily diagnostic mode to collect data on CNS compliance, perfusion, tissue $O_2$ saturation, and CSF production rate. In this mode, data may be transmitted via RF link for clinical use or may be used by the device to modify performance. The device may include operational modes where it maintains a flow or pressure set point and/or perfusion control. The device may include operational modes where it performs on a schedule based on time or other control inputs. Operation may be determined by patient position. The device may also be capable of following a programmed operational mode where the shunt mimics the pressure-flow performance of known shunts. The device may operate in any combination of these modes.

Given that a consistent problem with traditional shunts through the years has been occlusion, the present invention provides multiple device capabilities and characteristics that may contribute to occlusion prevention or reduction. Actuated valves, particularly thermo-fluidically driven valves, have higher closing pressures than do traditional passive valves and can prevent the accumulation of biological obstructions within the valve. Intermittent operation of the device will create higher operational flow rates and fluid sheer relative to known continuous flow valves, thus improving washout.

Designs comprise minimal or no fluidic dead spaces or comprise fully washed spaces which increase fluid shear and therefor the accumulation of materials which may comprise obstructions. In some embodiments occlusion rates are reduced by in vivo sterilization of valve mechanisms and/or devices which may be achieved by inductive or resistive heating of the fluidic systems associated with the implant. The power to heat the device may be delivered via the external source.

Some embodiments can also include the capability to communicate device failure or other clinically relevant information to the user or clinician, as determined from a control input sensor or the processed sensor data Some of the embodiments described herein can be used in addition as a replacement for traditional shunts when more control over CSF outflow is required, and/or, the novel shunt devices described below will accurately and safely provide an adjustable, programmable, consistent CSF flow and turnover rate to significantly improve metabolite clearance, prevent over-shunting, and treat the dementia, gait, and urinary disorders associated with NPH and AD.

In a first specific aspect of the present invention, an implantable body fluid drainage system includes a metering shunt having a housing with an internal chamber. A movable barrier divides the chamber into a first section and a second section, and the barrier can be displaced by a differential pressure. A first powered inlet valve providing a fill path to the first section of the chamber, and a first powered drain valve providing a drain path from the first section of the chamber. A CSF inlet conduit connects a CSF space to the first powered inlet valve. A CSF outlet conduit connects the first powered outlet valve to a discharge location. A controller opens the first powered inlet valve and close the first powered drain valve to fill the first section to a volume defined by the barrier and chamber geometry and closes the first powered inlet valve and opens the first powered drain valve to discharge the filled volume from the first section through the outlet conduit.

In specific embodiments of the first aspect of the present invention, the movable barrier is configured to elastically return to a non-displaced position in the absence of a differential pressure thereacross. In one variation of these embodiments, embodiments may further comprise a first powered bleed valve configured to connect the second section of the chamber to CSF pressure and a second powered bleed valve configured to connect the second section to a pressure of the discharge location. The controller will be further configured to (a) close the first powered bleed valve and open the second powered bleed valve to fill the first section and (b) open the first powered bleed valve and close the second powered bleed valve to discharge the filled volume from the first section through the outlet conduit. In other variations of these embodiments, the first powered inlet valve is a three-way valve configured to selectively connect either the first section or the second section of the chamber to CSF inlet conduit and wherein the first powered outlet valve is a three-way valve configured to selectively connect either the first section or the second section of the chamber to the CSF outlet conduit, wherein the controller is further configured to (a) position the first powered three-way inlet valve to deliver CSF from the CSF inlet conduit to the first section while blocking the second section from the CSF inlet conduit and (b) position the first powered drain valve to discharge the filled volume from the first section through the outlet conduit while blocking the second section from the discharge conduit.

In a second specific aspect of the present invention, a method for draining cerebrospinal fluid (CSF) in a patient comprises opening a first implanted inlet valve to fill a first section of a chamber in an implanted metering system with CSF and to displace a movable barrier isolating the first section the chamber from a second section of the chamber. The CSF flows into the first section in response to a differential pressure between CSF pressure and an outlet pressure, and a filled volume is defined by the barrier and chamber geometry. The first implanted inlet valve is closed and a first implanted outlet valve is opened to drain the filled volume of CSF from the first section to an outlet site wherein the barrier moves back to an original position to discharge the CSF from the first section. In this way, discrete, known volumes of CSF may be removed from the CSF space in a quantitative and controlled manner.

In specific embodiments of the second aspect of the present invention, the second section of the chamber is exposed to the outlet pressure while the first section is being filled with CSF. Usually, the first section of the chamber is exposed to CSF pressure while CSF is being drained from the first section, and the movable barrier is configured to elastically return to a non-displaced position in the absence of a differential pressure thereacross, such that the barrier initially displaces while the first section is filling with CSF, and the CSF is discharged by the force of the elated return of the barrier after opening the first implanted outlet valve and exposing the second section to CSF pressure. Typically, the movable barrier is configured to be displaced by the differential between the CSF pressure and outlet pressure when the second section is exposed to CSF pressure and the outlet valve is open, and the second section fills with CSF while CSF is being drained from the first section, and CSF is then drained from the second section to the outlet site while the first section is being filled with CSF. In all embodiments, CSF may be drained from the CSF space of the patient over a number of cycles to achieve a predetermined volume of CSF drainage.

BRIEF DESCRIPTION OF THE DRAWINGS

FIG. 1 illustrates a block diagram of a programmable metering shunt system incorporating an implantable portion and a non-implantable portion FIG. 2 illustrates a block diagram of a particular metering shunt system with power storage capability in the implant portion FIG. 3 illustrates a block diagram of another metering shunt system with no on board power storage in the implantable portion FIG. 8 is a table of the operating states of a two valve unit displacement metering component such as illustrate in FIG. 6 for use in a programmable metering system FIG. 9A illustrates a unit displacement fluidic metering component incorporating four on/off valves FIG. 9B illustrates a unit displacement fluidic metering component incorporating two two way valves FIG. 9C illustrates operating states for a unit displacement fluidic metering component incorporating two two way valves FIG. 10 illustrates an alternate circuit for a programmable metering shunt system comprising a two valve unit displacement fluidic metering component incorporating two on/off valves FIG. 11 illustrates a non-unit displacement fluid metering component for a programmable metering shunt system which comprises a single valve and two pressure transducers

FIGS. 23A and 23B illustrate two states of an on/off valve in which a diaphragm is displaced by a pumping a fluid across a boundary to occlude a fluid path and thereby to create a valve

DETAILED DESCRIPTION OF INVENTION

Figure 4:
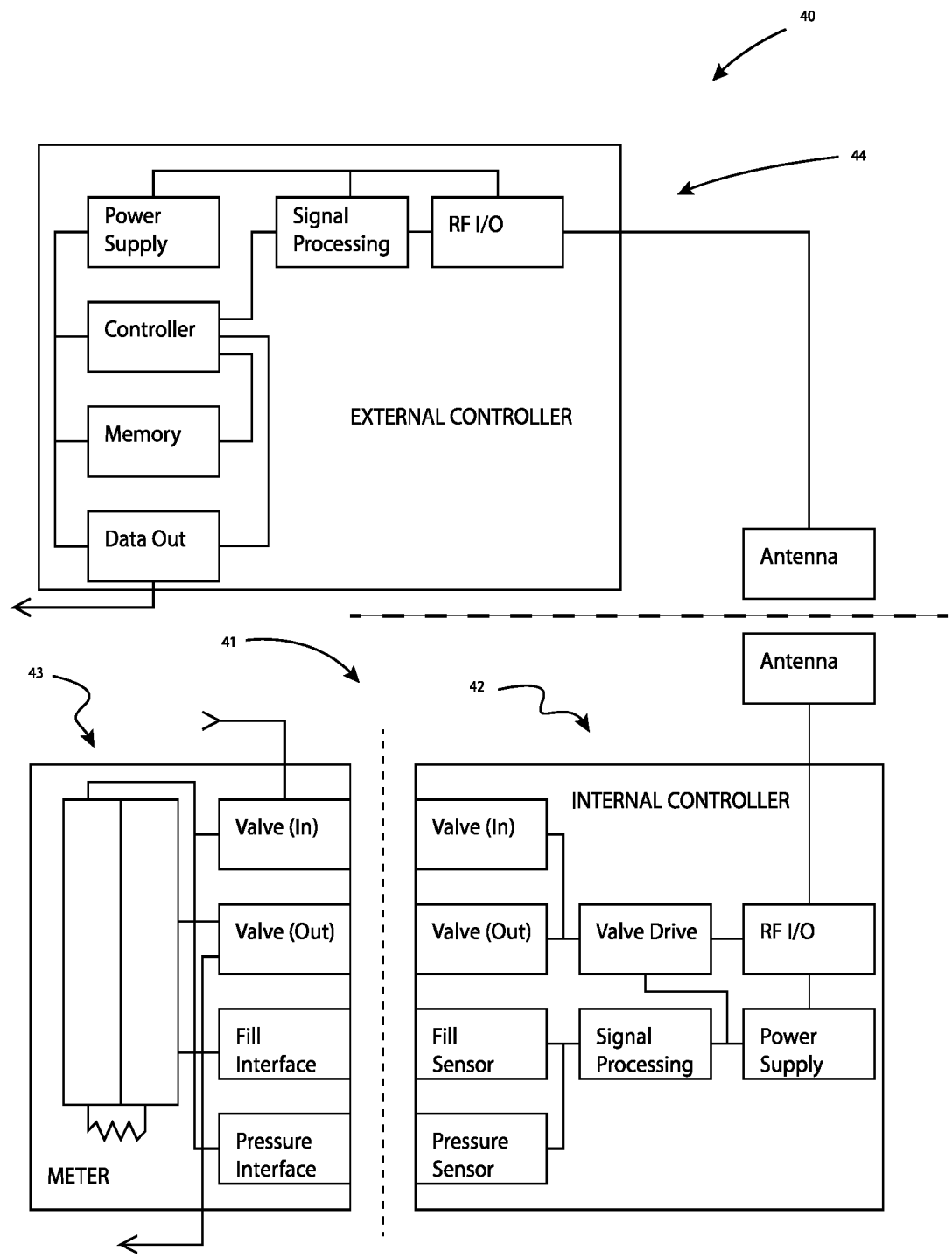
FIG. 4 illustrates a block diagram of a programmable metering shunt system incorporating a separate replaceable fluid handling component

FIG. 1 illustrates a generic programmable metering shunt system 10. The device comprises two primary components, an External Device (ED) 14 and an Internal Device (ID) 11. The ED 14 is used on the outside of the body and the ID 11 is implanted within the body. The ID 11 comprises an Internal Controller (IC) 12 and a Fluidics Device (FD) 13. The IC comprises an internal power source, a communications interface, and all control circuitry required to service the FD 13. The FD 13 comprises a meter which in turn is comprised of a metering chamber, and control valves. The FD 13 may additionally comprise sensors for monitoring pressure, device orientation, accelerations, chemical characteristics of the CSF, optical characteristics, electrical characteristics of the CSF, inputs associated with the environment, or other sensors.

FIG. 2 illustrates an embodiment of a programmable metering shunt system 20 in which an implantable device 21 comprises an electrical storage device. The internal long term storage device, such as a battery or high capacity capacitor, is charged via an RF link between an external device 24 and the internal device 21 across the patient's skin indicated by the dotted line. This same RF link may be used to communicate programming information to the ID 21 and or transmit data associated with ID 21 performance or measurements from the ID 21 to the ED 24. In such an embodiment the ID 21 would be charged via the ED 24 as needed. In some embodiments the ID 21 informs the ED 24 that it requires a charge when they are properly aligned. In this configuration the ID 21 can function for an extended period of time without being interfaced to the ED 24. In some embodiments the ID 21 can store diagnostic information during the periods when it is operating on internal power and transmit this information to the ED 24 when interfaced. In such a system there will be a processor and internal data storage on the ID 11. The data may comprise performance data, program data, and/or patient diagnostic data.

In alternate embodiments, the battery may be replaced with an atomic battery. In such an embodiment the RF link would be used to transmit data.

FIG. 3 illustrates an alternate programmable metering shunt system 30 in which there is no long term internal power storage device within the IC 32, such as a battery. Instead an ID 31 requires an ED 34 to be interfaced to an ID 31 for the system to operate. In such embodiments, the IC within 32 ID 31 may not require a processor.

In an hybrid embodiment of those described in FIGS. 2 and 3, a small battery may be included in the ID 11 which allows for operation of the diagnostic and data gathering capabilities but does not provide power to operate the meter.

FIG. 4 illustrates a detailed block diagram of a programmable metering shunt system 40 of the type described in FIG. 3. In this configuration, the meter is comprised of a metering chamber and two control valves. The system of FIG. 4 is also configured such that the portions of the system wetted by CSF, metering portion 43, are isolated and easily separable from an IC 42, thereby allowing for replacement of the IC without contacting the CSF space and risking a CNS infection.

Figure 5:
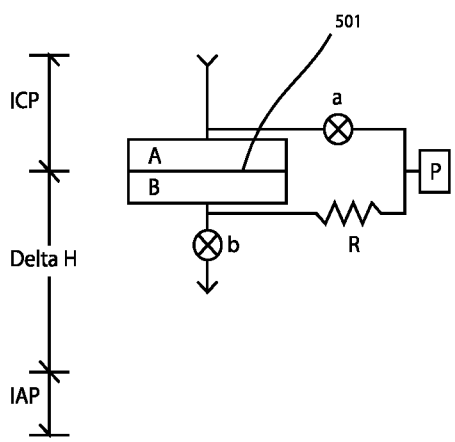
FIG. 5 illustrates a unit displacement fluidic metering component incorporating two on/off valves
Figure 6:
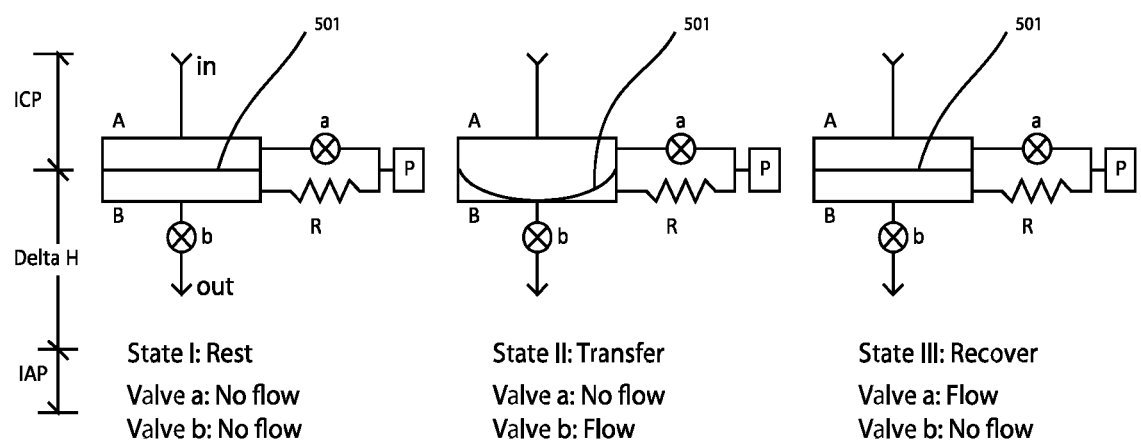
FIG. 6 illustrates functional states for a unit displacement fluidic metering component incorporating two on/off valves

FIG. 5 depicts a fluidics metering system useful in any of the systems described thus far. The line on the left indicates the various pressures acting across the metering device. These are the ICP, a Delta H equal to the hydrostatic head associated with the outflow conduit of the shunt system 20, and the Intra Abdominal Pressure (IAP) where the shunt system 20 is draining. IAP has been used as the outflow pressure because it is the most common outflow location; however in some situations the outflow will drain into another location in the body and the pressure at that location will replace the IAP. The meter is comprised of two chambers A and B separated by an elastomeric membrane or moveable barrier 501, two valves "a" and "b", a pressure transducer P and an optional fluid resistor R. FIG. 6 depicts the meter of FIG. 5 in each of its three operational states. Starting from the left, the meter is in the Rest position in which all valves are in a no flow position (closed). In this configuration chambers A and B are isolated from one another and there is no flow through the device. When valve "b" is switched to the flow configuration (opened) the device shifts into the Empty configuration. In this configuration the pressure across the diaphragm drives the diaphragm from the rest position into chamber B, displacing the fluid in chamber B out the outflow conduit until the movable barrier 501, e.g. a diaphragm, reaches the bottom of chamber B at which point flow stops. At this point the volume of fluid displaced by the diaphragm has been metered across the device. When valve a is then closed and valve b opened, the barrier is allowed to return to its rest position through optional resistor R. Valve "a" is then closed and valve "b" opened so that the system is returned to its rest configuration. The transitioning through these three configurations, Rest, Empty, Recover, comprises one metering cycle in which a unit or bolus or volume is transferred.

Figure 7:
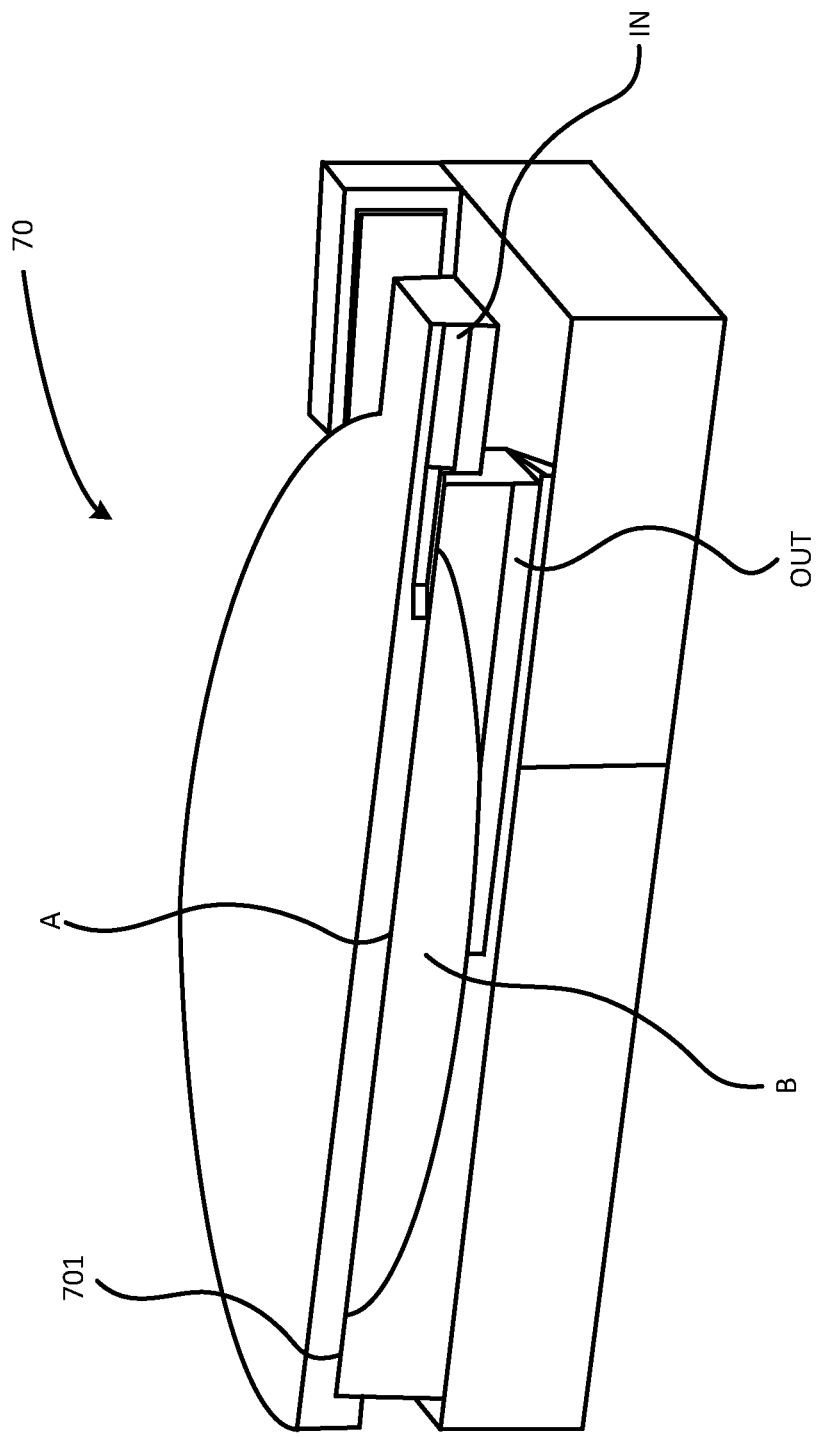
FIG. 7 illustrates a cross sectional view of an embodiment of a programmable metering shunt system comprising a two valve unit displacement fluidic metering component incorporating two on/off valves

Given a design in which the diaphragm displaces a known and consistent amount for any differential pressure greater than some minimum, the transferred bolus will be of constant volume. Therefore, total flow is the count of cycles times the bolus volume, and a precise record of flow can be maintained by recording the time at which each transfer occurs and or a count of occurrences. Such a design is comprised in an elastomeric membrane displacing into a spherical section as depicted in the sectional view of a programmable metering shunt system 70 illustrated in FIG. 7. In FIG. 7, a barrier or diaphragm 701, in the rest position, sits against the top of the chamber, and the volume of chamber A is very small. When the meter is shifted into the Empty configuration the diaphragm shifts and conforms with the spherical bottom surface of chamber B and the volume of chamber A becomes that of chamber B in the Rest or Recover configuration. These chambers are substantially different than an accumulator, as described by U.S. Pat. No, 6,689,085 or 20030004495A1, in that the fluid transfer in the chamber is mediated by loads applied across a membrane separating the two chambers and the input and output valves reside in different locations to those described in the prior are and therefore provide for a different function than.

Using a 5 mil thick silicone elastomeric membrane approximately 1.2 inch in diameter such a design can be configured to transfer consistent volumes of approximately 1 mL under a minimum operating pressure of 5 cm of water. Allowing ICP to go much below 5 cm of water may be dangerous for the patient. The table in FIG. 8 summarizes four possible states for the valves in the configuration described in FIG. 6.

In this meter configuration the recovery from the Empty position to the Recover configuration is in part mediated by the energy stored in the elastomeric diaphragm. The elastomeric membrane in alternate embodiments may be replaced by a spring loaded piston, or a spring loaded in an elastic membrane configured to match the shape of the chamber.

FIG. 9A depicts and alternate design which comprises four valves 904 and which does not require energy storage in a diaphragm 901. In this design valves 'a" and" a'" and "b" and "b'" are cycled such that a and a' are in one state and b and b' are in the opposite state. As depicted, inlet 902 interfaces with a location within the ICP and outlet 903 with a location in the IAP. The table in FIG. 9A characterizes the valve states associated with the operation the meter.

An alternate embodiment illustrated in FIG. 9B requires two two-way valves 905. If "a", "b", "a'", and "b'" are taken as fluid paths, the adjoining state table of FIG. 9A represents the operation of the meter of FIG. 9B. The chambers used in the embodiment of FIG. 9 or any others embodiment herein described may comprise a spherical shape as described in FIG. 7 or any other shape which consistently limits the travel of the movable barrier at a predetermined minimal pressure differential.

An alternative programmable metering shunt system 100 is depicted in FIG. 10. A primary distinction between the systems of FIG. 5 and FIG. 10 is that valve b is located between the inlet and chamber A. The valve depicted in FIG. 10 is functionally similar performance to the valve in FIG. 5 and the outcomes are also represented in FIG. 8.

FIG. 11 represents a chamberless meter with two pressure sensors and single valve. In this configuration, known pressure conditions and valve resistance can be used to calculate volumetric flow through valve "a". This design variation offers potential size advantages but is much more sensitive to variation in pressure measurement and valve resistance with reference to compiling flow data.

Figure 12:
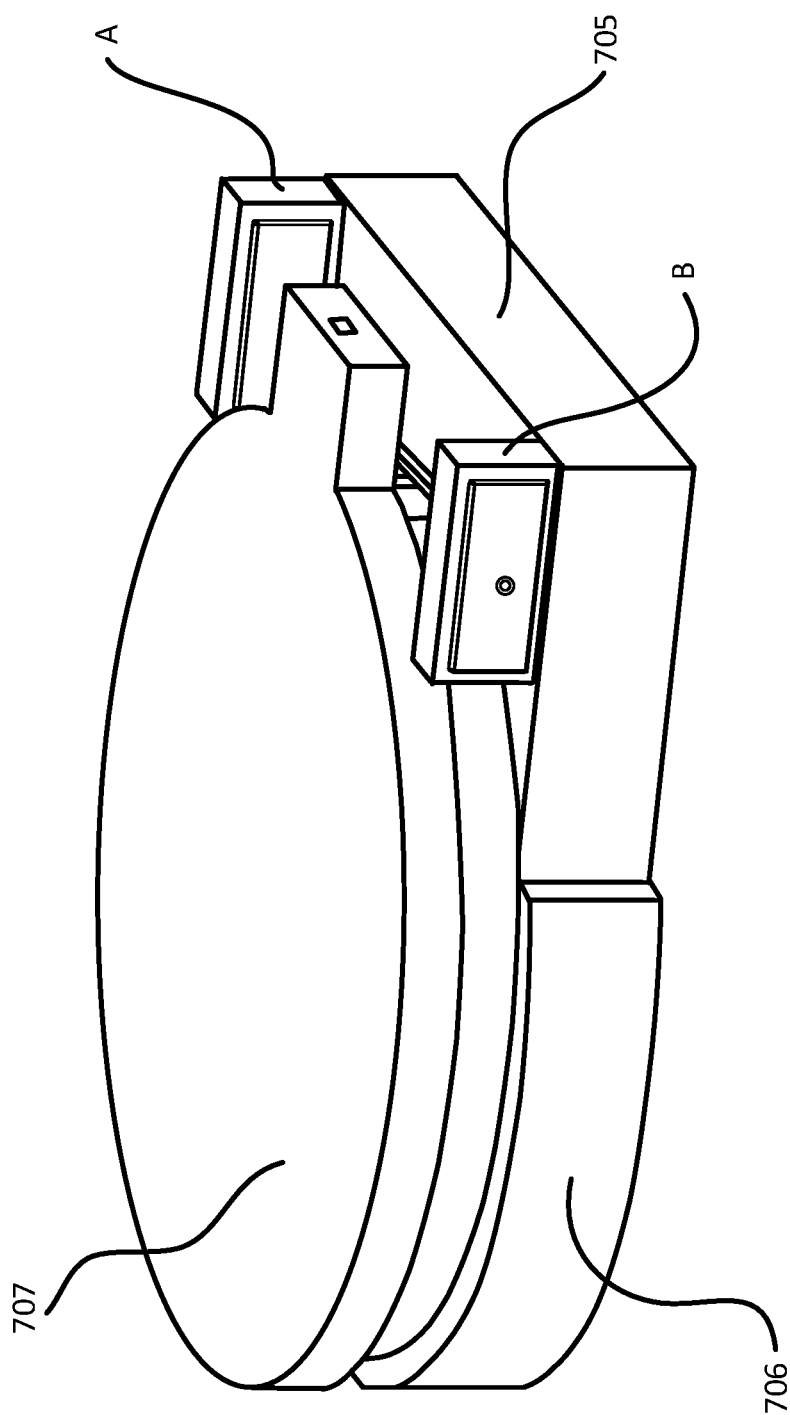
FIG. 12 illustrates a full view of the embodiment of a programmable metering shunt system illustrated in FIG. 7
Figure 13:
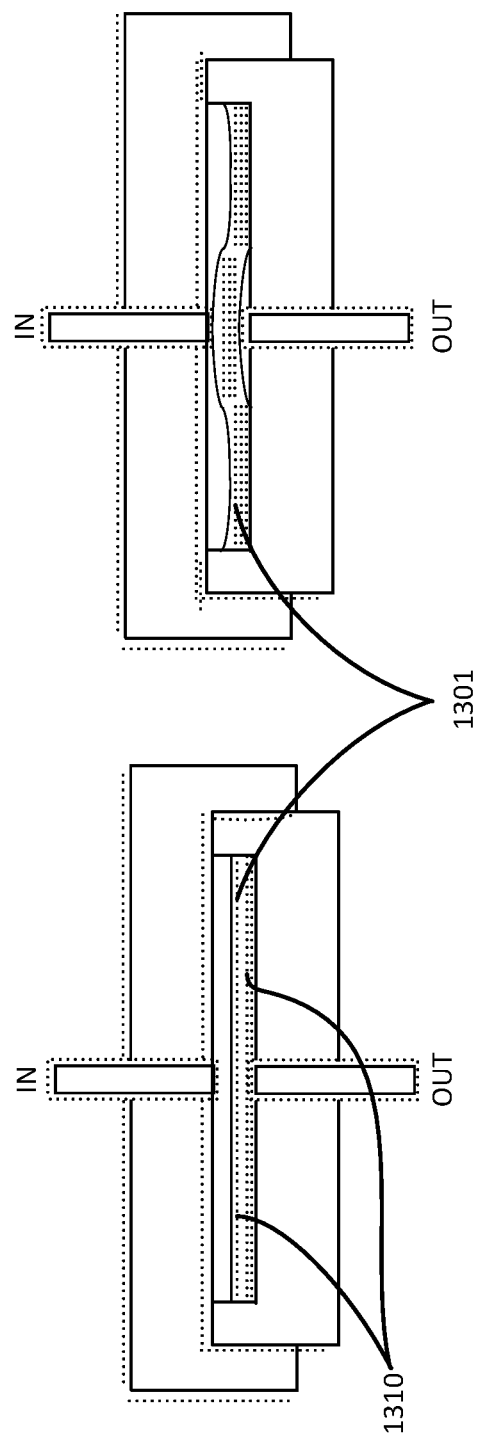
FIG. 13 illustrates two states for an/off fluidic valve comprising a diaphragm deformed by a thermally driven memory material

FIG. 12 is an illustration of the primary components in an implantable meter, roughly the size of a neuro-stimulator comprising the meter 707, battery 705, and IC 706, as described in FIGS. 6 and 7. Valves A and B for this design are depicted in FIG. 13 in both an open and closed state. Valves are activated by applying and electrical current to a Nitinol® wire (not shown) embedded close to the bottom surface in a diaphragm 1301 and spanning the two anchor wires 1310. When the Nitinol wire is heated by the passage of current it shrinks forcing the diaphragm 1301 to bow away from the outflow port on aperture in the valve. Fluid is then allowed to flow around the outer perimeter of the diaphragm from the inflow to the outflow. As pictured a minimal positive pressure differential across the valve, In-to-Out or Out-to-In, will force the valve to close, hence in an un-energized condition the valve acts as a check valve and impedes flow.

Figure 14:
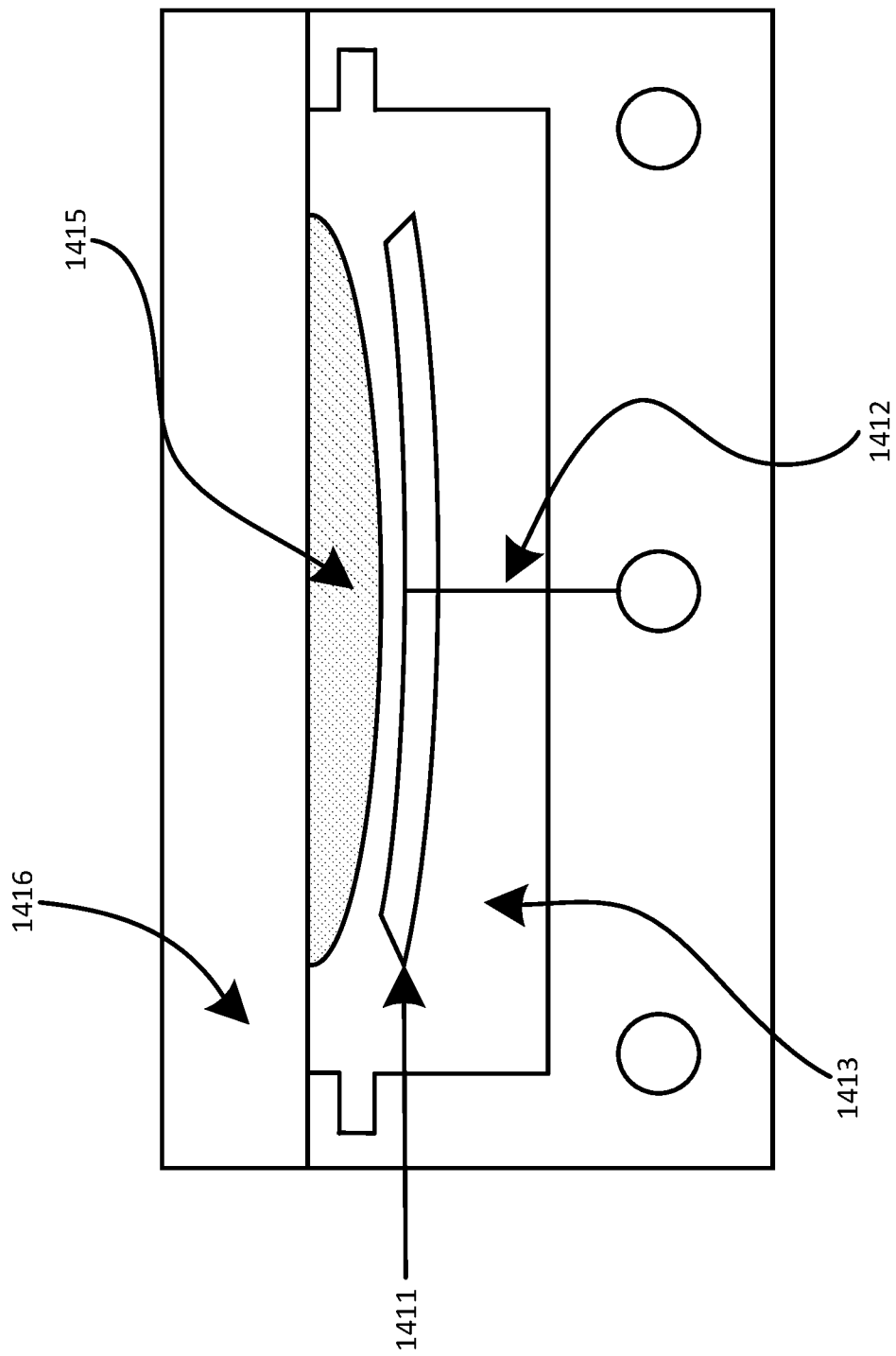
FIG. 14 illustrates an on/off planer fluid valve in an open state, deformed by a thermally driven memory material
Figure 15:
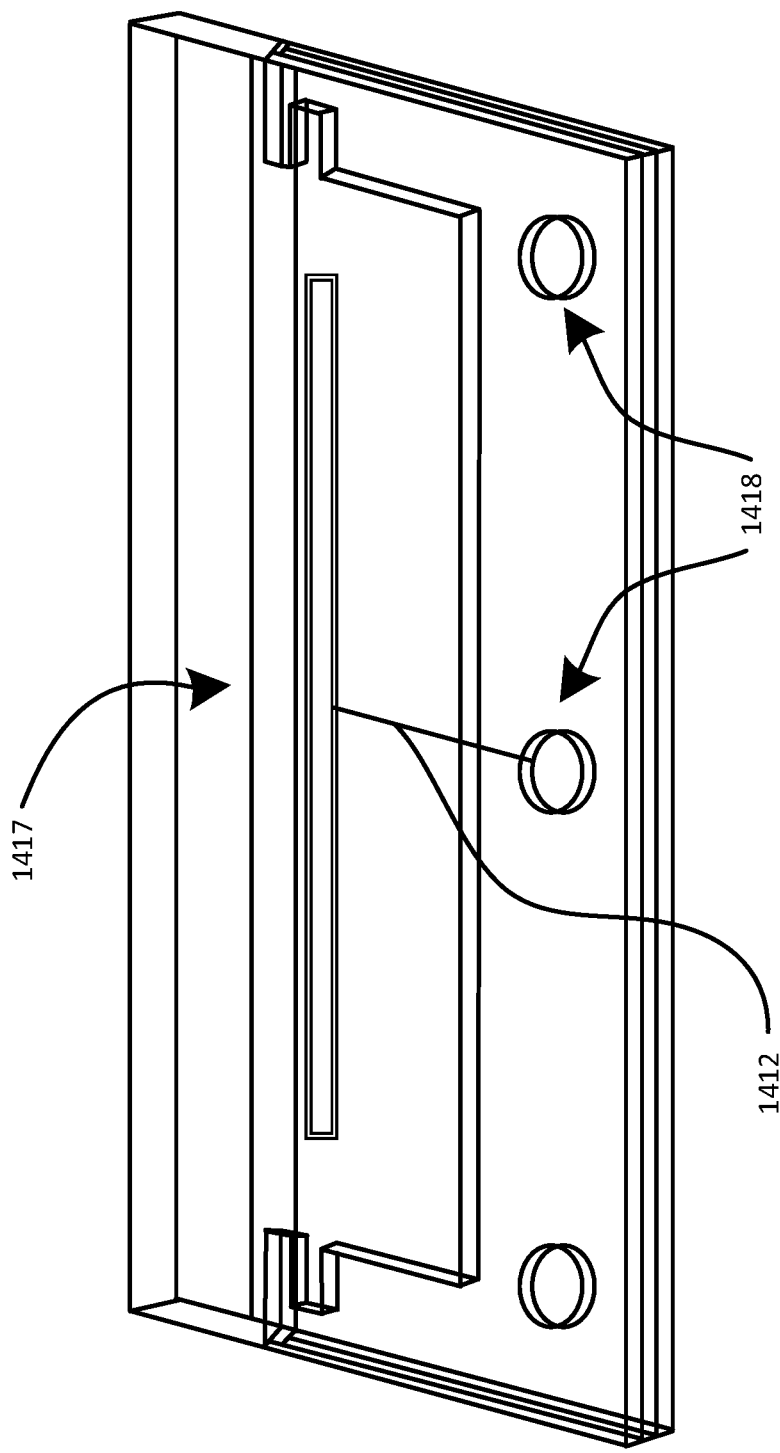
FIG. 15 illustrates an isometric of the valve of FIG. 14 in a closed state

FIGS. 14 and 15 depict two views of an alternate valve embodiment. The valve in FIG. 14 consists of a Nitinol® wire 1412 connected to an anchor 1411 and a rigid polymer support structure 1416, encased within a silicone membrane 1413. The Nitinol® 1412 wire in this configuration can be thermally heated by application of a current resulting in joule heating of the wire, causing a contraction of the wire and the displacement of the anchor and membrane. The silicone membrane 1413 and a portion of the support structure adjacent to the anchor 1411 define an orifice 1415. The support structure 1416 at this location presents a planar face which does not mechanically constrain the silicone which remains separable from the support structure upon activation. On the remaining three sides, the geometry of the support structure 1416 is designed to mechanically constrain the silicone membrane using through holes 1418, as depicted in FIG. 15. In this manner, the orifice is passively closed but opens to allow flow when the silicone membrane is displaced by activation of the Nitinol® wire. FIG. 14 depicts this valve in the active and open configuration. The forces required to open such a valve configuration is relatively insensitive to the differential pressure across the valve In the configuration depicted in FIG. 14, the anchor is pre-stressed before the silicone is cast around it. This preloading allows the Nitinol® wire 1412 to return to its original (pre-contraction) length between contractions bu contributing a restoring force to close the valve. The Nitinol® wire may be fixed to the pre-stressed beam with epoxy, mechanically looped around it, or both. In this configuration a loop of Nitinol wire is used such that the sourcing and power delivery elements are static and not limited in size and thereby conductance by the other requirements of the structure.

Figure 16:
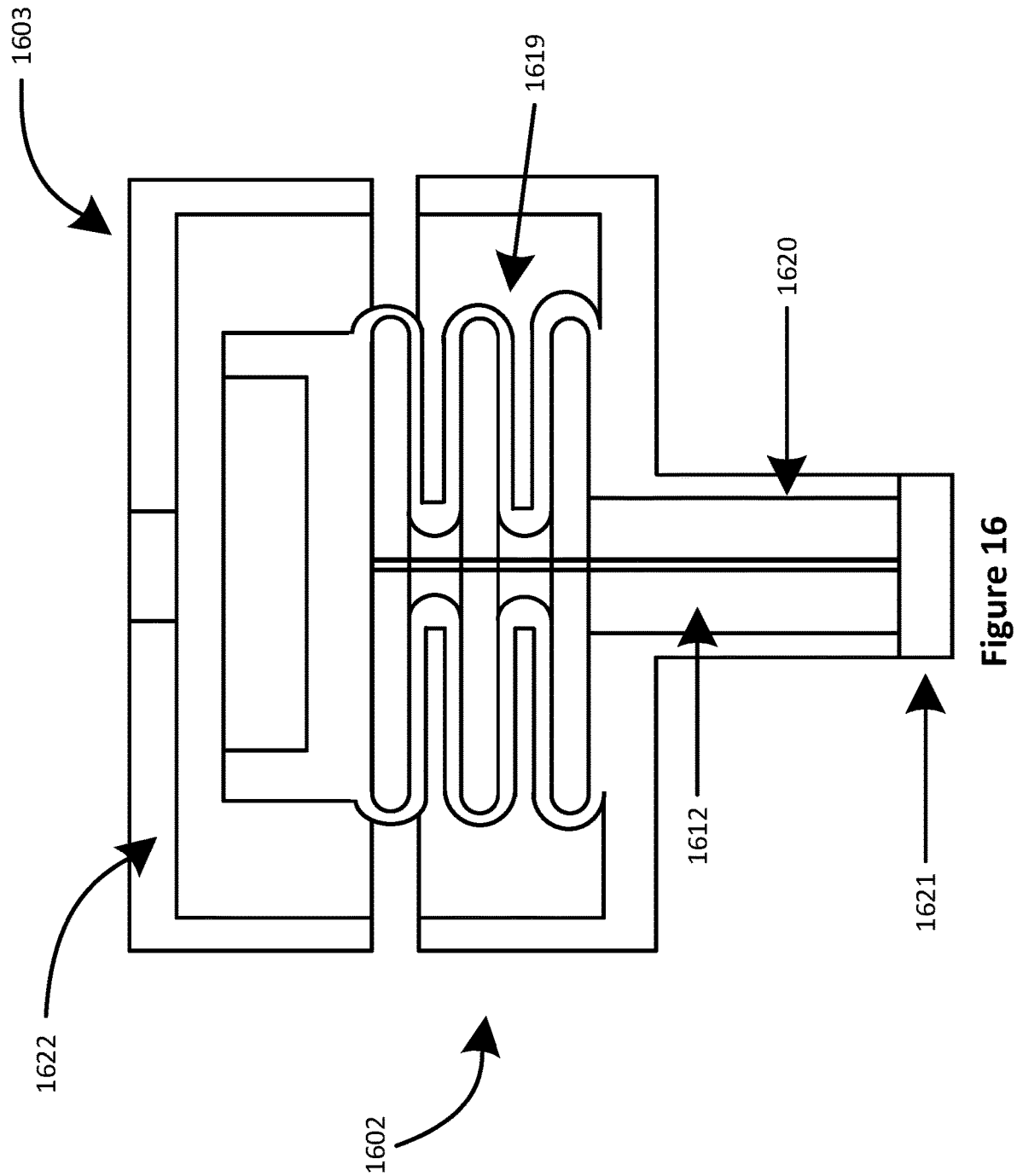
FIG. 16 illustrates a thermally driven valve incorporating a thermally driven wire and a bellows

FIG. 16 depicts a valve consisting of a Nitinol® wire 1612 embedded in thermally insulated chamber 1620. Part of this chamber consists of a flexible or expandable bellows 1619, allowing for the wire to contract when electrically activated. One end of the insulating chamber 1620 is connected to a face and forms a valve with an opposing face. When thermally activated, the wire 1612 contracts, compresses the bellows 1619, and displaces the end of the chamber and the valve face 1622 connected to it. The valve face can be configured so that an active displacement either opens or closes the valve. FIG. 16 depicts a configuration where the active displacement allows a flow between the two faces and a transfer of fluid between an inlet 1602 and outlet 1603. As depicted, one end of the Nitinol® wire is electrically coupled to the structure and the other insulated from the structure by a non-conducting material 1621, allowing it to be electrically activated.

One advantage of the configuration depicted in FIG. 16 is the thermal isolation of the Nitinol® wire 1612. Thermally isolating the wire in an insulated chamber 1620 can significantly reduce the thermal losses relative to a wire embedded in a membrane. Potential methods of insulation include a sealed vacuum or aerogel material. Such efficiencies influence the useful life of the shunt.

Such high precision valves with a flexible bellows can be fabricated in the sub millimeter regime using a layered construction processes such as those marketed by Microfabrica Inc of Van Nuys, Calif. Alternatively, laser sintering or other 3D printing techniques may be used. In such a design and fabrication method, the valve element tolerances critical to performance may be maintained as all elements are fabricated together and thereby no assembly tolerances are introduced.

The volumetric or linear expansion of additional solid materials can be employed in a analogous manner to the Nitinol® wire depicted in FIGS. 13-16. Volumetric or linear expansion may be thermally driven using a material's coefficient of thermal expansion, a change in a metals atomic lattice structure, or a change in the bonding and crosslinking of polymer structures. One possible embodiment of a polymer actuators employs "artificial muscles", which consist of one or many Nylon® filaments with a torsion preload and or writhe. Such filaments are capable of producing linear displacements through contraction when heated. In such a design, heating may be induced by a resistive wire coiled with the polymer or by exposure to an external source Energy expenditure can be reduced by a valve with a latching mechanism or multiple stability points. Such a valve would require power to transition between an open and closed state, but require no power to maintain either the open or closed state. This is distinct from the valve described in FIG. 14, which requires power to transition from a closed state and maintain an open state, but requires no power to return to the closed state and maintain the closed state.

Figure 17:
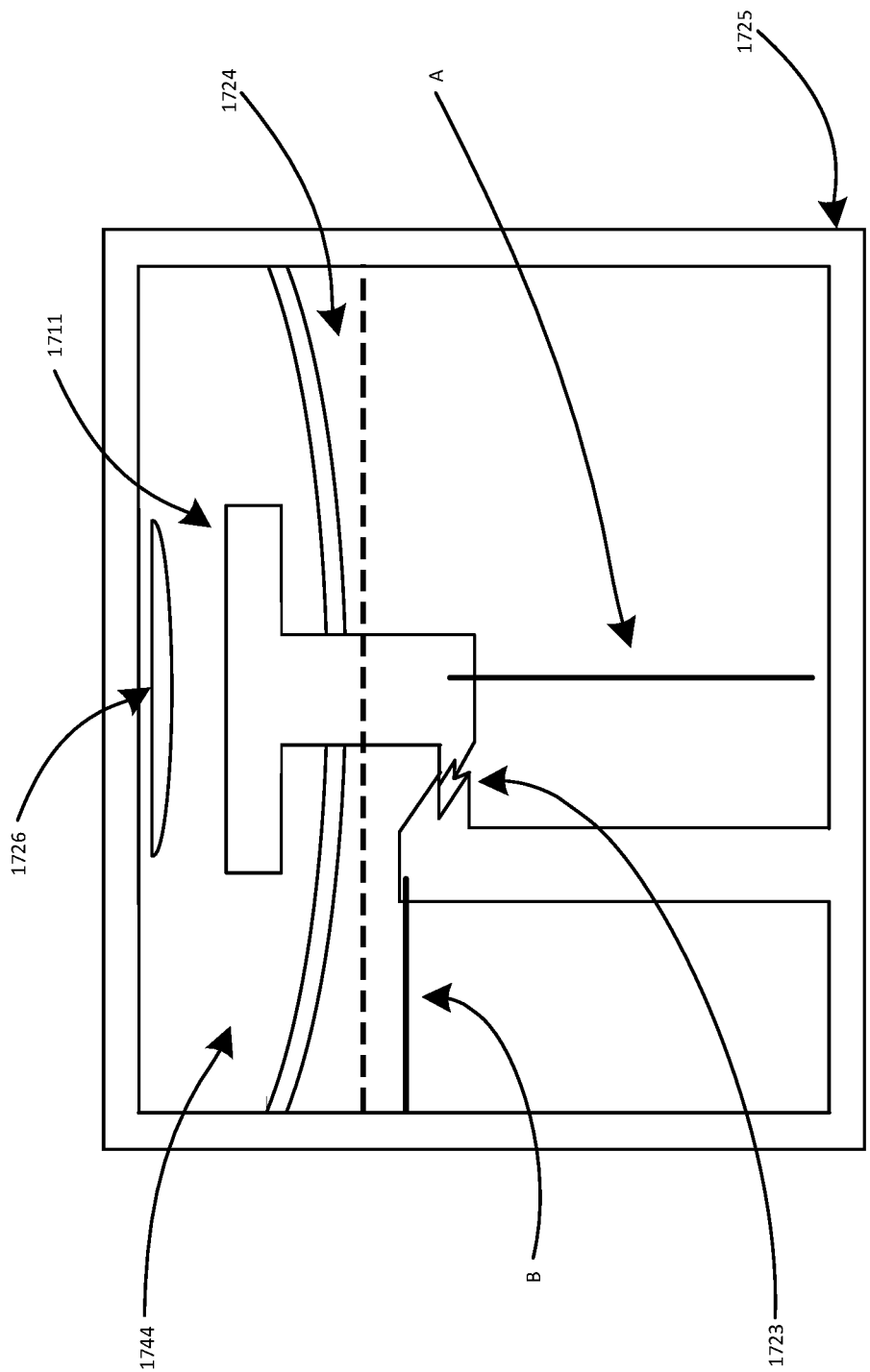
FIG. 17 illustrates a planer on/off valve incorporating a latch

An exemplary embodiment of a latching valve is given in FIG. 17. Such a valve can be manufactured by casting a silicone membrane 1724 within a. rigid polymer structure 1725. Features of this valve include a slit valve 1726, an anchor structure 1711, a latching mechanism 1723, and two actuators A and B. When actuator A contracts, the anchor structure 1711 comprising spring element 1744, which is embedded in a silicone membrane, is displaced and a slit valve is opened. As the anchor structure 1711 is displaced, the latching mechanism 1723 serves to hold the anchor in a displaced position when actuator A is no longer powered. When actuator B contracts, the latching mechanism 1723 disengages the anchor structure 1711 and a restoring force provided by the silicone membrane 1724 and anchor structure 1711 returns the anchor structure to the original position, closing the slit valve 1726. The valve remains in this position when actuator B is no longer powered.

Figure 18:
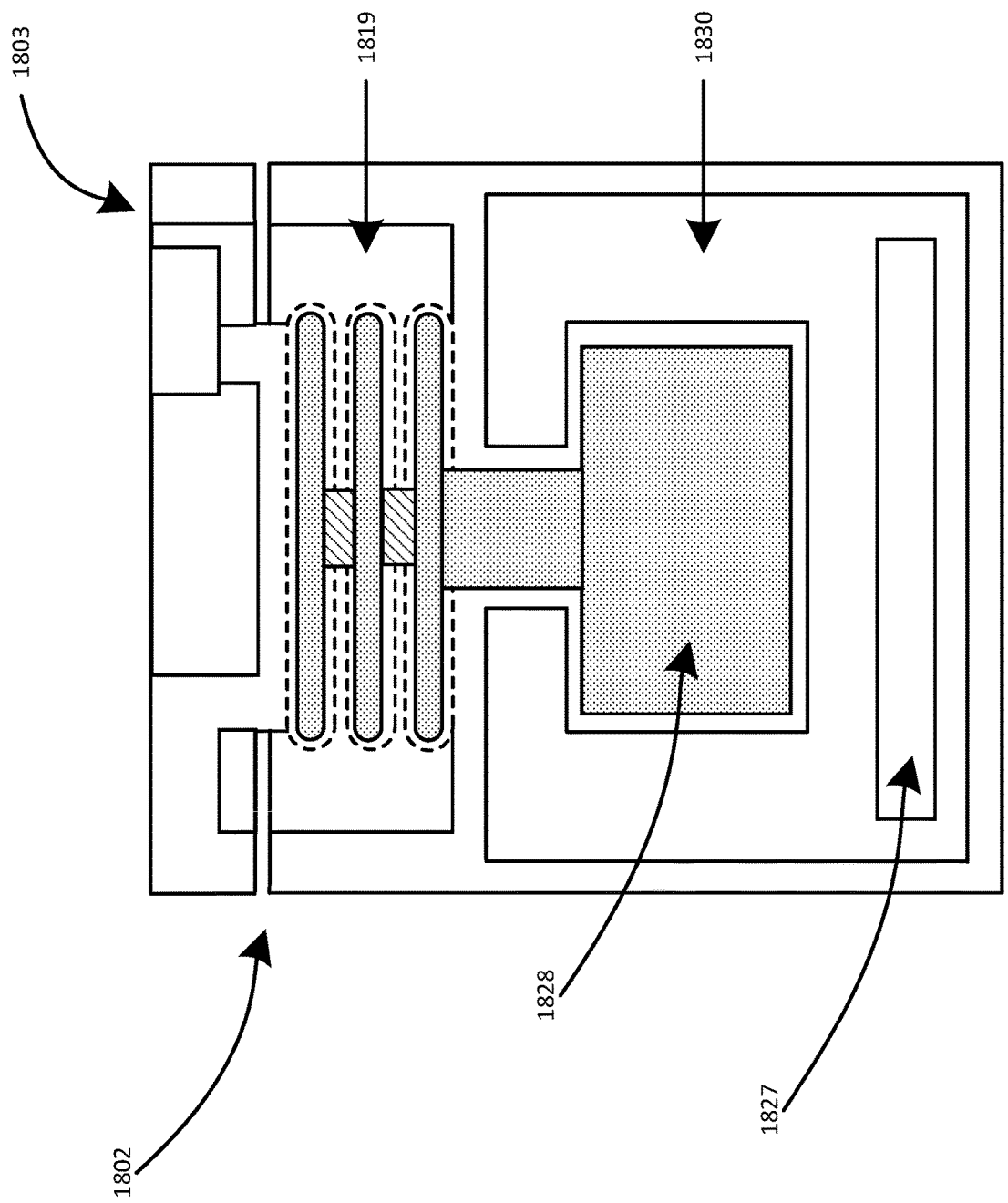
FIG. 18 illustrates an on/off valve driven by a thermally driven change in volume of the material with in the bellows

A fluidically driven valve variation of valve 16 is depicted in FIG. 18. This valve differs from that depicted in FIG. 16 primarily in the means of actuation. In FIG. 18, the Nitinol® wire is replaced by fluid which expands when heated, such as silicone oil. Thermal expansion of this fluid can be achieved by inductive or resistive heating elements and results in an expansion of the bellows, and the displacement of a valve face. When inductive heating is used micro or nano particles of a ferromagnetic material such as magnetite may be introduced into the silicone oil. In the configuration depicted in FIG. 16, the active displacement of the face opens the valve to allow flow between an inlet and an outlet.

In FIG. 18, a volume of fluid 1827 which is inductively heated is located in a reservoir 1828 and isolated from the volume contained within a bellows 1819 by narrow mechanical constriction which limits thermal conduction. This is significant because the large surface area of the bellows greatly increases the rate of conductive and convective heat transfer. By increasing the thermal resistance between the two volumes, the energy consumption of the valve 1802 and the amount of heat transferred to the CSF is greatly reduced.

Figures 19A, 19B:
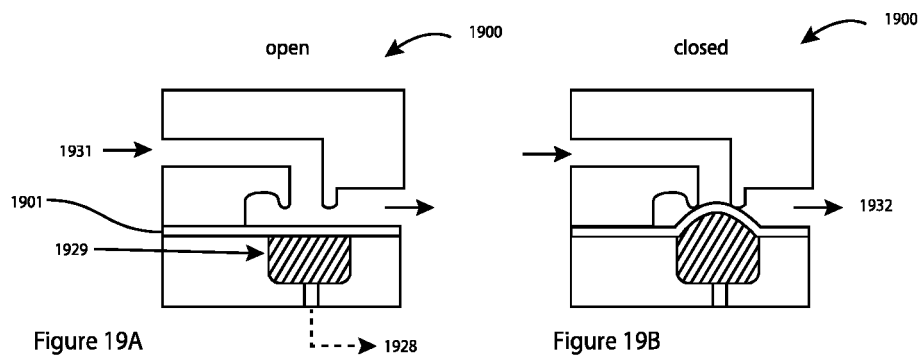
FIGS. 19A and 19B illustrate two states of an on/off valve in which a diaphragm is displaced by a contained material to activate the valve
Figures 20A, 20B:
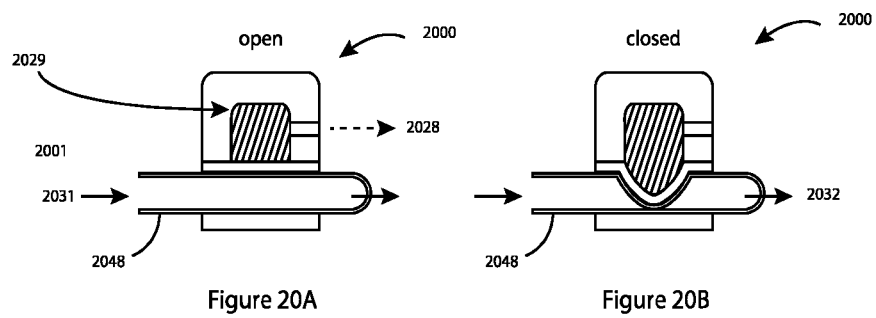
FIGS. 20A and 20B illustrate two states of an on/off valve in which a diaphragm displaced by a contained material is used to compress a tube thereby to create a valve
Figures 21A, 21B:
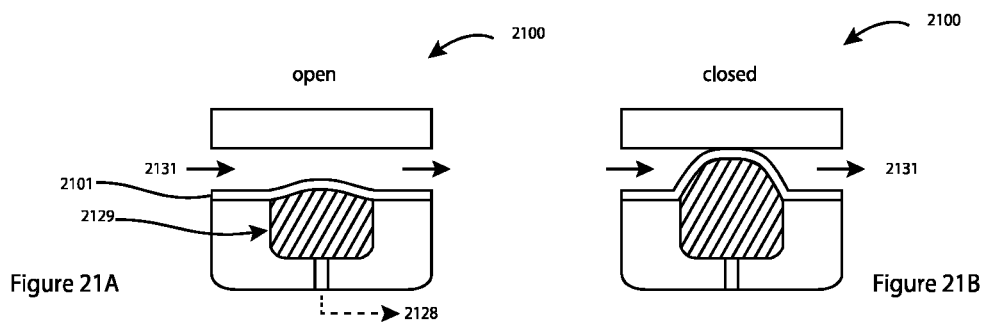
FIGS. 21A and 21B illustrate two states of an on/off valve in which a diaphragm displaced by a contained material is used to occlude a fluid path and thereby to create a valve

A fluidically driven valve 1900 is illustrated in an open configuration in FIG. 19A and in a closed configuration in FIG. 19B. The previously described bellows structure is replaced by a diaphragm 1901 to form a deformable fluid chamber 1929. The internal volume can be deformed by thermal expansion of a fluid in the chamber or in a connected reservoir (not shown). Deformation and/or displacement of the diaphragm 1901 forms a seal with an adjacent orifice, as depicted in FIG. 19. Such displacement may be transmitted through an intermediate structure (not shown) to reduce or prevent flow 1932. In an alternate embodiment, a fluidically driven valve 2000 has a diaphragm adjacent to a constrained tube 2048 in open (FIG. 20A) and closed (FIG. 20B) configurations, respectively. The tube is collapsed and thereby obstructed by the deflection of the diaphragm 2001 or deformable structure. One advantage of this structure is that it introduces minimal complexity to the flow path 2031 of the CSF and reduces the risk of obstruction. Alternatively, the diaphragm 2101 can be incorporated into the wall of a flow pathway within a valve 2100, as depicted in FIGS. 21A and 21B.

One significant advantage of fluidically operated valves is the ability to operate with higher opening and closing pressures than Nitinol® actuated devices. This can prove advantageous to sealing the valve and the disrupting biological matter which may begin to accumulate in the valve orifice, thereby reducing the chance of occlusion. Other advantages of this configuration include the ability to vary valve displacement and thereby valve fluid resistance by altering either or both the initial volume and temperature of the fluid reservoir. When a larger fluid volume is contained in the reservoir a mechanical gain is exhibited.

Figures 22A, 22B:
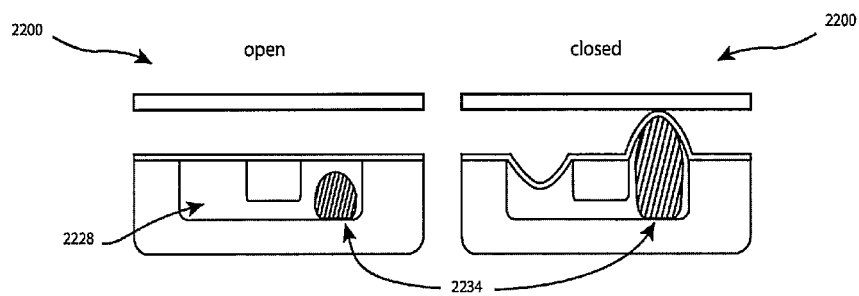
FIGS. 22A and 22B illustrate two states of an on/off valve in which a diaphragm is displaced by a hydrogel expansion occlude a fluid path and thereby to create a valve

An alternate valve embodiment 2200, illustrated in FIGS. 22A and 22B corresponding to open and closed configurations, comprises a hydrogel structure that displaces a diaphragm or membrane to create a valve. Hydrogels are water saturated structures and can be formulated to expand and/or contract in response to thermal or electrical stimulation. The volumetric expansion of a hydrogel requires the hydrogel to draw fluid from an external location. Fluid volume 2228 contains the hydrogel 2234. As the fluid in chamber 2228 is either heated or an electrical field is applied across the hydrogel 2234, by means not shown, the hydrogel is caused to expand thereby closing the fluid path as illustrated in FIG. 22B.

Figures 23, 23B:
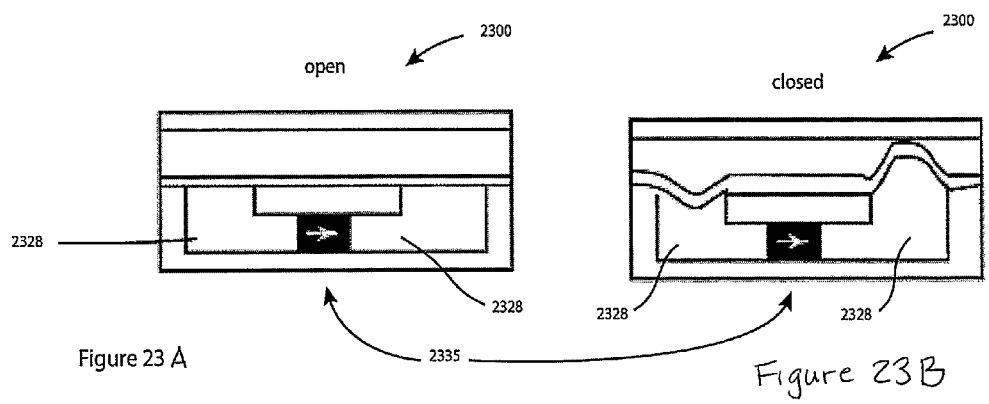
Figure 24:
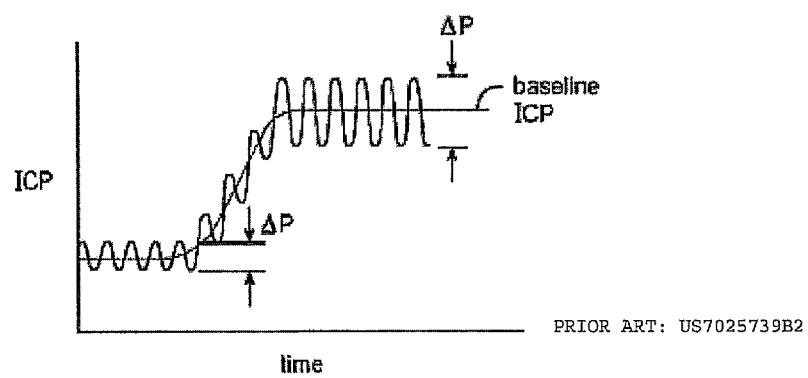
FIG. 24 illustrates a prior art presentation of a relationship between CNS compliance and pressure variations in ICP associated with blood pressure FIG. 25 illustrate a pressure flow performance curve associated with a hydrocephalus shunt the performance of which are duplicable by systems described herein FIG. 26 illustrate a pressure flow performance curve duplicable by systems described herein FIG. 27 illustrate a pressure flow performance curve duplicable by systems described herein FIG. 28 illustrate a pressure flow performance curve duplicable by systems described herein

FIGS. 23A and 23B illustrate a valve comprising an electro osmotic pump 2335 to move a volume of fluid between two compliant chambers 2328. This change in volume can be accommodated by the diaphragms or membranes which also act as valve seats.

In alternate embodiments an electro osmotic pump can be used to drive valves as configure in FIGS. 19 and 20 via optional ports 1928 and 2028 respectively.

Potential pump mechanisms for driving fluids a in pump-operated valves include but are not limited to electro-osmotic pumps, electrostatic pumps, Nitinol® actuated pumps, and pumps driven by the thermal expansion of a solid or fluid.

Clinical parameters such as ICP, IAP, CSF production, CNS compliance may be measured by the devices described herein and used in device control algorithms or for clinical review or diagnostic purposes. Some of the measurement capabilities of the devices of FIGS. 1 and 5 include a flow meter as and/or a pressure sensor, as noted below.

ICP may be measured by having the patient in a recumbent posture facing up. In this posture the pressure transducer and ventricle will be at approximately the same level. To effect the measurement valve "b" is closed and valve "a" is open, as indicated by the recovery position depicted in FIG. 6. In this configuration pressure transducer P measures the pressure on the upstream side of the diaphragm in the ventricle. IAP may be measured in much the same fashion, however, with valve "a" closed and valve "b" open CSF production may also be estimated in this setting as follows. An initial ICP0 value is measured as described above. This may comprise an average value acquired over an initial period of time. The meter then transfers a known volume of CSF from input to output in a minimum of time. ICP is then again measured and monitored over time. After removal of the CSF the ICP will fall and production can be estimated by dividing the known transferred volume of CSF by the time it takes for the ICP to return to the ICP0 value.

When the patient is in any posture, active or still, ICP and Delta H+IAP can be measured and logged for future review during the normal cycling of the meter. ICP is measured when the meter is in the Recover configuration and ΔH+IAP when the meter is in the Transfer configuration. CNS compliance can be measured by monitoring the change in pressure as a function of drained CSF volume.

CSF production can be measured by the procedure of monitoring a baseline ICP, then draining a predetermined volume of CSF, measuring the reduced TCP, and then recording the increase in ICP as a function of time. The CSF production rate is then the volume drained/time to regain baseline ICP. The pressure/drainage cure can additionally be used to estimate CNS compliance.

Figure 25:
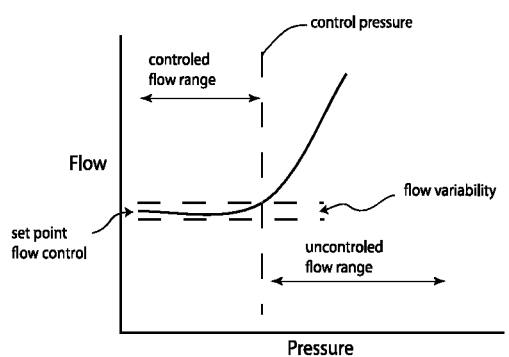

CNS compliance may additionally be determined by the pressure specific modification of the cardiac and respiratory components of the ICP waveform as depicted in FIG. 25 and described in U.S. Pat. No. 7,025,739. The amplitude of these waveforms components can be, in some cases isolated by band pass filtering, associated with mean/baseline ICP to create a patient specific pressure-compliance curve. This data may then be used as a device control parameter and/or relayed to clinicians. Similarly, the frequency of the cardiac and respiratory components may be isolated in order to measure pulse rate and respiratory rate.

One or more sensors on the ventricular catheter may collect additional data, which may be stored for clinician review or incorporated into a feedback mechanism for metering control. One exemplary metric of interest is blood perfusion, which may be measured by photo-plethysmography (PPG) or bioimpedence sensors located on the ventricular catheter in the parenchyma or at the burr hole. Low perfusion caused by elevated ICP is a dominant mechanism for neural damage in hydrocephalus and the direct measurement of perfusion rates may present a valuable input for flow control feedback.

In some embodiments, photoplethysmography and or O2 saturation measurements may be performed by sensors mounted in the ventricular catheter.

A real time clock in the controller can record the duration of and/or between fluid transfers, the duration of and/or between data collection, and the time of day.

When an O2 sensor or plethysmography sensor are included in a metering system as described herein, an exemplary control strategy comprises metering of CSF when low perfusion is detected. Metering may be discontinued if perfusion levels return to desired level if a predetermined volume of CSF has been transferred or if there is no effect on perfusion arising from a predetermined transfer of CSF. Hybrid flow control strategies may be desirable using a combination of perfusion and ICP measurements. Such a strategy could start or stop the transfer of CSF when either an ICP or perfusion condition is reached or require both conditions to be reached for action The device may also be operated as a set point flow, pressure, or perfusion controller to maintain CNS characteristics at a constant level or within a defined range.

An additional operational mode may be the metering of CSF on a schedule determined by time of day or any combination of available sense inputs. Two exemplary embodiments of this would be the metering of CSF at night and conditionally metering CSF at night if the patient is also in a horizontal position.

The device may also be programmed to operate with a linear or non-linear pressure dependent flow response which would be equivalent to the pressure flow performance of shunt with a constant or variable fluid resistance.

Figure 26:
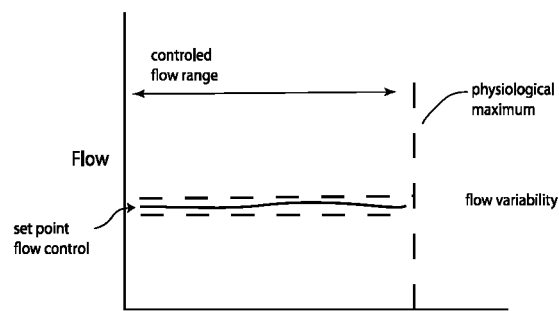
Figure 27:
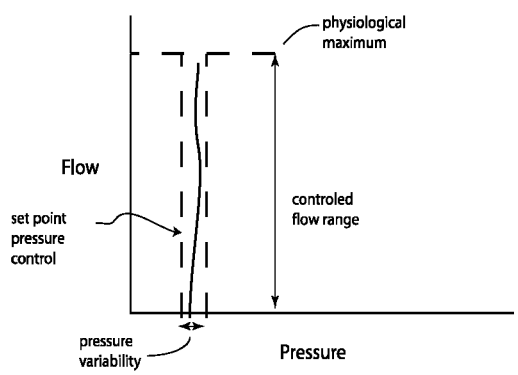
Figure 28:
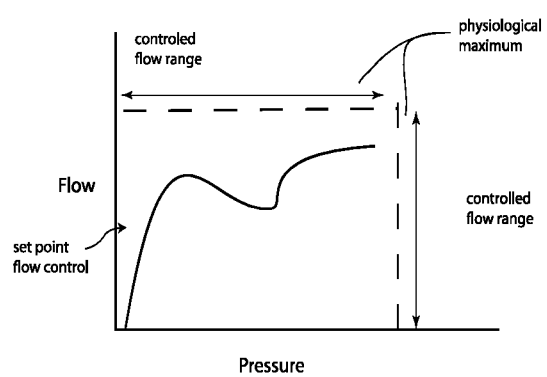

FIGS. 25 through 28 illustrate multiple pressure flow performance curves each of which embodiments of the metering systems described herein are capable of duplicating. FIG. 25 depicts the general pressure dependent flow control available with commercially available static flow control shunts, such as the OSVII from Integra Neurosciences. FIG. 26 depicts a set point flow control performance. Within the controlled flow range, flow rate is independent of pressure and the device is capable of maintaining the controlled flow range across all pressures physiologically possible in a patient. This flow rate can be set at any constant within the operational range and remain constant. Set point pressure control can vary flow rate to maintain a desired pressure as depicted in FIG. 27. Hybrid modes between set point pressure and set point flow control can define any performance curve that lies within the controllable pressure and flow ranges, such as that depicted in FIG. 28. Additionally, flow and pressure control regimes can be changed as a function of variables such as time or position or posture and these characteristics allow for treatment methods previously unavailable to clinicians.

The embodiments described herein allow performance characteristics for a given shunt to be redefined by clinicians by downloading a new program to the implanted shunt, eliminating the need for many shunt revisions.

The devices described herein, due to the intermittent operating of the meters, will experience higher operational flow rates and fluid shear relative to known continuous flow valves. Furthermore, known transfer volumes and operational response times will better control the range of flow conditions experienced within the device and allow for more accurate computational modeling of flow through the system and reduce dead spaces.

In some embodiments described herein in-vivo thermal sterilization of the shunt, part of the shunt or its valves is achieved by the use of resistive or inductive heating of elements or materials within the shunt and the transmission of this heat within the shunt. This is achieved by resistive or inductive coupled heated elements within the shunt system or a specific sub-domain of the shunt. In some embodiments these elements may be the same as those used to actuate the valves or pumps within the shunt. In some embodiments this feature may only be available when the shunt is connected to an external power source or the power is directly applied by an external source in a clinical setting.

Figure 29:
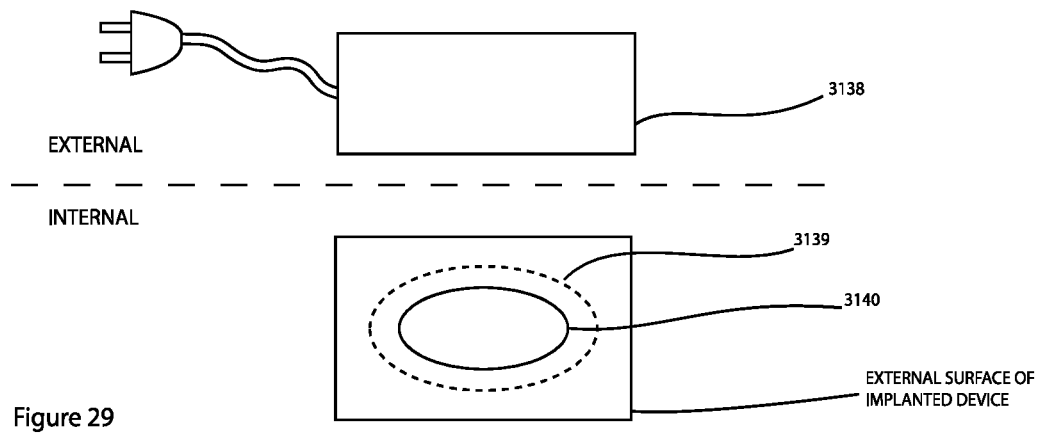
FIG. 29 illustrates a programmable fluid metering shunt system comprising an RF power coupling link and the ability to generate heat in an implantable portion of the implanted portion of the system for use in killing infectious organisms which have colonized within the implantable portion

One exemplary embodiment is depicted in FIG. 29 where an external inductive energy source 3138 is used to heat magnetite particles within an implanted device. FIG. 29 depicts an embodiment where the magnetite particles are only located in a sub-domain or layer 3139 encompassing the wetted surfaces 3140 within the shunt. In this manner, the thermal resistance between the heated sub-domain and the tissues of the patient are increased.

Figure 30:
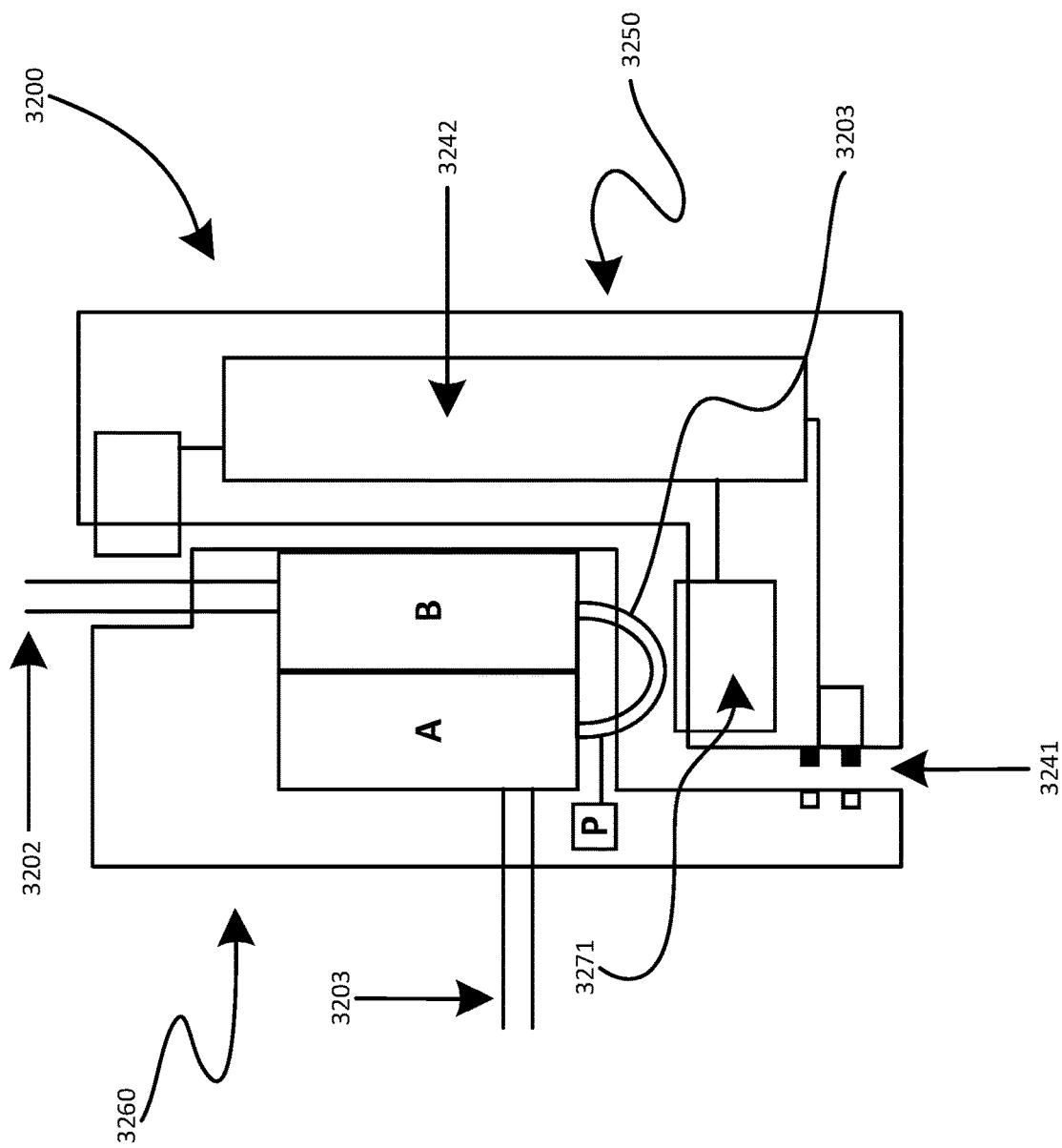
FIG. 30 illustrates an embodiment for the implantable portion of the programmable fluid shunt system of FIG. 4

FIG. 30 depicts an embodiment of a programmable metering shunt system 3200, as described in FIG. 10, which incorporates many of the features described herein. The device in FIG. 30 consists of two sub components which can be fixed together when implanted and replaced independently in the case of revision or failure. One "wetted" component 3260 contains all of the CSF wetted surfaces comprising, inflow port 3202 and outflow port 3203, as well as the metering chambers A and B. The other "dry" component 3250 comprises all the implanted electronics with power source 3242 and valves "a" and "b". The inflow valve depicted in this embodiment are comprised of a portion of inflow tubing 3202 which are collapsed and obstructed by expanding element such as described in FIG. 20 above. The outflow valve is comprised of tubing 3203 which in turn is obstructed by a second expanding element 3271 similar to that described in FIG. 20. The expansion elements comprised in the valves of this embodiment may alternatively be comprised any of the other drive mechanisms previously described. Power and data communications may be transferred from the dry component to the wetted component via electrical connection 3241.

What is claimed is:

1. A method for estimating a patient parameter in a patient having a cerebrospinal fluid (CSF) metering shunt implanted to drain CSF from the patient's central nervous system (CNS), said method comprising:
measuring an initial intracranial pressure value of the patient;
removing a known volume of CSF from the patient's CSF space using the CSF metering shunt;
determining at least one of (1) a change in intracranial pressure (ICP) of the patient and (2) a time it takes for the intracranial pressure to return to the initial intracranial pressure value, after the known volume of CSF has been removed; and
calculating at least one of CSF production rate or CNS compliance based upon the value of the known volume and the value of the determined change in ICP and/or time.

2. A method for estimating a patient parameter as in claim 1, wherein the patient parameter comprises a CSF production rate calculated by dividing the known volume of CSF by the time it took for the intracranial pressure to return to the initial intracranial pressure value to estimate the CSF production rate in the patient.

3. A method for estimating a patient parameter as in claim 1, wherein the patient parameter comprises a CNS compliance calculated as a ratio of the known volume of CSF removed and the change in ICP.

4. A method for estimating a patient parameter as in claim 1, wherein the initial ICP measurement consists of a single measurement.

5. A method for estimating a patient parameter as in claim 1, wherein the initial ICP pressure measurement comprises an average value acquired over a period of time.

6. A method for estimating a patient parameter as in claim 1, wherein ICP is measure with a sensor implanted upstream of the implanted CSF metering shunt.

7. A method for estimating a patient parameter as in claim 1, wherein removing the known volume of CSF from the patient's CSF space using the CSF metering shunt to reduce the intracranial pressure comprises controlling the implanted pump using an external device outside of the body.

8. A method for estimating a patient parameter as in claim 7, wherein the external device controls the implanted CSF metering shunt to open a first implanted inlet valve to fill a first section of a chamber in the implanted metering shunt with CSF and to displace a movable barrier isolating the first section the chamber from a second section of the chamber, wherein the CSF flows into the first section in response to a differential pressure between CSF pressure and an outlet pressure and wherein a filled volume is defined by the barrier and chamber geometry, and closing the first implanted inlet valve and opening a first implanted outlet valve to drain the filled volume of CSF from the first section to an outlet site wherein the barrier moves back to an original position to discharge the CSF from the first section.

* * * * *